(12) United States Patent
Barkan et al.

(10) Patent No.: US 11,195,275 B2
(45) Date of Patent: Dec. 7, 2021

(54) METHODS TO INDUCE NON-RIGID MESH TRANSFORMATION IN-VARIANCE TO CNN BASED MEDICAL IMAGING CLASSIFIERS

(71) Applicant: International Business Machines Corporation, Armonk, NY (US)

(72) Inventors: Ella Barkan, Haifa (IL); Alon Hazan, Toronto (CA); Daniel Khapun, Haifa (IL); Vadim Ratner, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 96 days.

(21) Appl. No.: 16/654,035

(22) Filed: Oct. 16, 2019

(65) Prior Publication Data
US 2021/0118127 A1   Apr. 22, 2021

(51) Int. Cl.
| | |
|---|---|
| *A61B 5/00* | (2006.01) |
| *A61B 5/055* | (2006.01) |
| *A61B 8/08* | (2006.01) |
| *A61B 90/00* | (2016.01) |
| *G06N 3/08* | (2006.01) |
| *G06T 11/00* | (2006.01) |
| *G06T 7/00* | (2017.01) |
| *G06T 7/168* | (2017.01) |

(Continued)

(52) U.S. Cl.
CPC .......... *G06T 7/0012* (2013.01); *A61B 5/0053* (2013.01); *A61B 5/055* (2013.01); *A61B 5/7267* (2013.01); *G06N 3/08* (2013.01); *G06T 7/168* (2017.01); *A61B 2090/374* (2016.02); *A61B 2090/378* (2016.02)

(58) Field of Classification Search
None
See application file for complete search history.

(56) References Cited

U.S. PATENT DOCUMENTS

| | | | |
|---|---|---|---|
| 6,169,817 B1 * | 1/2001 | Parker | G06T 7/11 382/131 |
| 2010/0016710 A1 * | 1/2010 | Kumar | A61B 8/0841 600/425 |

(Continued)

OTHER PUBLICATIONS

Duan et al., "Volume Preserved Mass-Spring Model with Novel Constraints for Soft Tissue Deformation," IEEE J Biomed Health Inform . Jan. 2016;20(1):268-80. doi: 10.1109/JBHI.2014.2370059. Epub Nov. 12, 2014. (Year: 2014).*

(Continued)

*Primary Examiner* — Soo Shin
(74) *Attorney, Agent, or Firm* — Gregory J. Kirsch (57) ABSTRACT

Embodiments of the present systems and methods may provide techniques that are applicable to a variety of imaging modalities and that utilize prior knowledge of the dynamics of a physiological system to analytically generate augmented samples for machine learning. For example, in an embodiment, a method implemented in a computer comprising a processor, memory accessible by the processor, and computer program instructions stored in the memory and executable by the processor, the method may comprise generating a transform for an image of tissue based on deformation of the tissue under compression, obtaining an image of tissue using an imaging modality, and generating an output image by transforming the image of the tissue using the transform.

14 Claims, 8 Drawing Sheets

(51) Int. Cl.
*G16H 30/40* (2018.01)
*G16H 50/20* (2018.01)

(56) References Cited

U.S. PATENT DOCUMENTS

| | | | | |
|---|---|---|---|---|
| 2010/0067769 | A1* | 3/2010 | Neemuchwala | G06T 7/344 |
| | | | | 382/132 |
| 2011/0112549 | A1* | 5/2011 | Neubach | A61B 90/11 |
| | | | | 606/130 |
| 2013/0150704 | A1* | 6/2013 | Vitek | A61N 7/02 |
| | | | | 600/411 |
| 2014/0071125 | A1* | 3/2014 | Burlina | G06T 17/00 |
| | | | | 345/420 |
| 2015/0379422 | A1 | 12/2015 | Chandler | |
| 2016/0005169 | A1* | 1/2016 | Sela | G09B 23/30 |
| | | | | 382/131 |
| 2016/0203630 | A1* | 7/2016 | Pai | G06T 13/40 |
| | | | | 345/473 |
| 2018/0247156 | A1 | 8/2018 | Holtham et al. | |
| 2019/0325572 | A1* | 10/2019 | Mansi | A61B 5/1079 |

OTHER PUBLICATIONS

Wang et al., "An Unfixed-elasticity Mass Spring Model based simulation for soft tissue deformation," 2014 IEEE International Conference on Mechatronics and Automation (Year: 2014).*
Olaf Ronneberger et al., "U-Net: Convolutional Networks for Biomedical Image Segmentation", arXiv, May 18, 2015.
Erik Andersson et al., "Evaluation of Data Augmentation of MR Images for Deep Learning", Mater Thesis, Faculty of engineering, Centre for Mathematical Sciences, Lund University, 2018.

* cited by examiner

METHODS TO INDUCE NON-RIGID MESH TRANSFORMATION IN-VARIANCE TO CNN BASED MEDICAL IMAGING CLASSIFIERS

BACKGROUND

The present invention relates to techniques that provide a transform for an image of tissue based on information relating to deformation of the tissue under compression.

Machine learning models, such as Deep Neural Network (DNN) models, are in widespread use in many areas of computing, such as in processing medical images. To use such a model, the model must be trained using an amount of training data that is sufficient to achieve the desired model accuracy and generalization. Often, such amounts of training data are difficult to obtain, or may even be unavailable. Current methods for dealing with the lack of data to train classifier models are insufficient.

Typically, models for medical imaging are trained to process particular tissue types. Prior knowledge of the tissue dynamics of such tissue types may be incorporated to improve classifier generalization. When training a DNN model to classify a medical image, in order to deal with small datasets, different standard data augmentation methods are typically applied. However, these methods do not generally consider the true physical properties of the tissue, which can vary.

Medical imaging modalities often involve physical transformation of the tissue being imaged, such as compression, stretching, translation, etc. Current data augmentation methods are typically very general and not domain specific, and further may require learning the transformations of tissue images. These methods do not consider the true physical properties of the tissue, which can vary. Likewise, conventional techniques, instead of learning the augmentation, may learn a spatial transformation as part of the classification task. However, this is typically limited to specific predefined transformation families and still does not consider medical imaging priors. Other conventional automatic augmentation transformation learning methods may use Generative Adversarial Networks to find minimal label flipping transformations, which may produce useful training samples to make the classifier more robust.

Thus, conventional techniques try to improve augmentations for different domains using machine learning and may parameterize some given transformation, which is very general. Further, conventional techniques may assume large labeled datasets when learning a transformation, which are usually not actually available.

Accordingly, a need arises for techniques that are applicable to a variety of imaging modalities and that utilize prior knowledge of the dynamics of a physiological system to analytically generate augmented samples for machine learning.

SUMMARY

Embodiments of the present systems and methods may provide techniques that are applicable to a variety of imaging modalities and that utilize prior knowledge of the dynamics of a physiological system to analytically generate augmented samples for machine learning. Embodiments may utilize additional physical information relating to transformation of the tissue being images. Embodiments may incorporate prior knowledge of the tissue dynamics to improve classifier generalization.

For example, in an embodiment, a method implemented in a computer comprising a processor, memory accessible by the processor, and computer program instructions stored in the memory and executable by the processor, the method may comprise generating a transform for an image of tissue based on deformation of the tissue under compression, obtaining an image of tissue using an imaging modality, and generating an output image by transforming the image of the tissue using the transform.

In embodiments, the imaging modality may generate an image with an associated elastogram and the transform may be generated by modeling the tissue as a rectangular grid of masses connected by springs based on the elastogram and generating a displacement over the rectangular grid with a constrained bottom, wherein the displacement minimizes a total potential elastic energy with respect to the positions of all the masses, except the top and bottom masses, which induce compressional pressure. The imaging modality may generate an image without an associated elastogram and the transform may be generated by generating an elastogram based on exemplary images with elastograms, modeling the tissue as a rectangular grid of masses connected by springs based on the elastogram, and generating a displacement over the rectangular grid with a constrained bottom, wherein the displacement minimizes a total potential elastic energy with respect to the positions of all the masses, except the top and bottom masses, which induce compressional pressure. The imaging modality may comprise one of ultrasound or magnetic resonance imaging. The imaging modality may generate an image without an associated elastogram and the transform may be generated by learning the transform based on a plurality of images of a same tissue imaged with different levels of applied pressure and on the associated applied pressure information. The output image may be further generated based on information indicating a pressure applied to the tissue during acquisition of the image of the tissue. The imaging modality may comprise one of mammography or tomography.

In an embodiment, a system may comprise a processor, memory accessible by the processor, and computer program instructions stored in the memory and executable by the processor to perform generating a transform for an image of tissue based on deformation of the tissue under compression, obtaining an image of tissue using an imaging modality, and generating an output image by transforming the image of the tissue using the transform.

In an embodiment, a computer program product may comprise a non-transitory computer readable storage having program instructions embodied therewith, the program instructions executable by a computer, to cause the computer to perform a method comprising generating a transform for an image of tissue based on deformation of the tissue under compression, obtaining an image of tissue using an imaging modality, and generating an output image by transforming the image of the tissue using the transform.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION

Embodiments of the present systems and methods may provide techniques that are applicable to a variety of imaging modalities and that utilize prior knowledge of the dynamics of a physiological system to analytically generate augmented samples for machine learning. Embodiments may utilize additional physical information relating to transformation of the tissue being images. Embodiments may incorporate prior knowledge of the tissue dynamics to improve classifier generalization.

For example, Mammography and Tomography may include "Applied Pressure" information, while Ultrasound and Magnetic Resonance Imaging (MRI) may include "Elastogram" information. This information may be useful to produce pressure induced transformations of tissue images.

Figure 1:
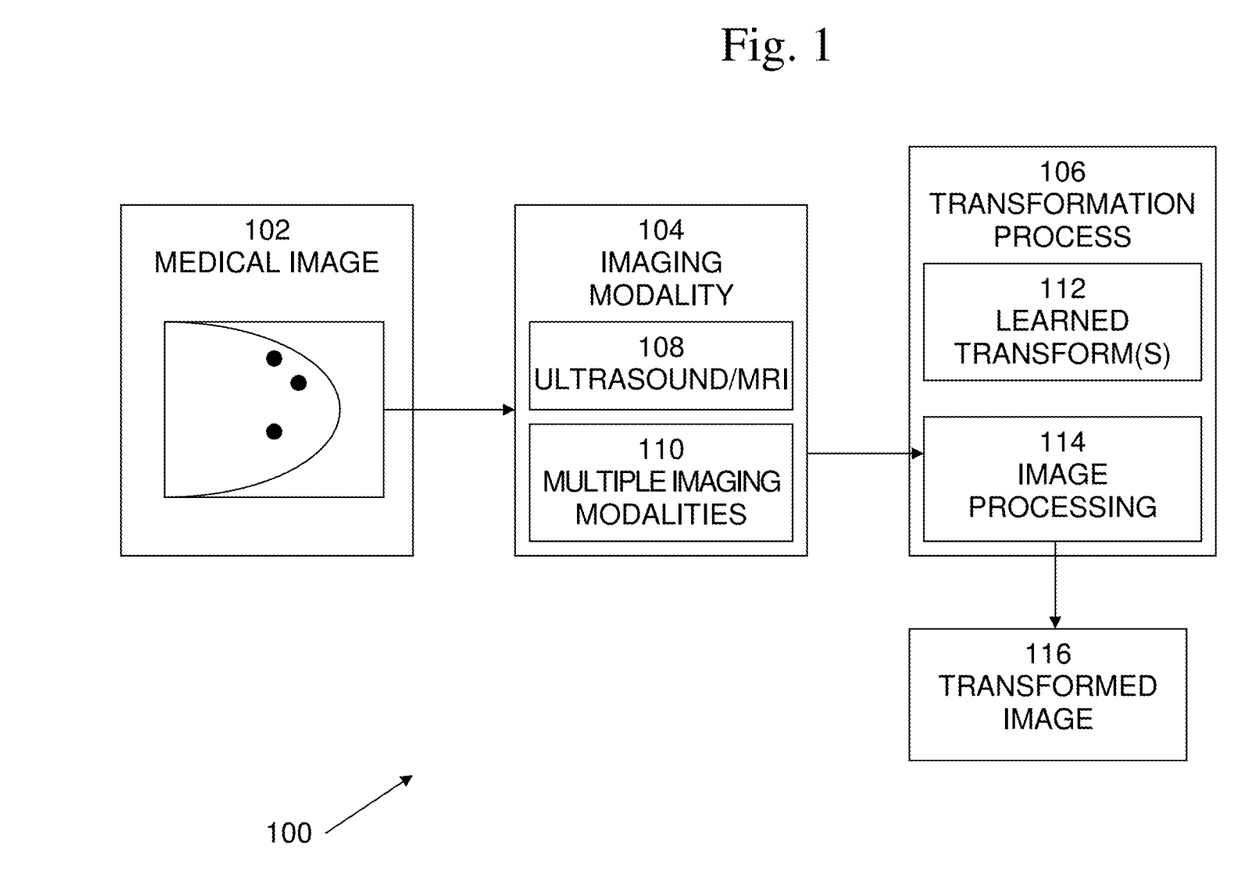
FIG. 1 is an exemplary block diagram of processing system according to embodiments of the present techniques.

An exemplary block diagram of a processing system according to embodiments of the present techniques is shown in FIG. 1. As shown in this example, one or more medical images 102 may be obtained using imaging modalities 104 and may be processed by transformation process 106. Imaging modalities may include, for example, ultrasound and MRI imaging 108, as well as multiple imaging modalities 110, such as Mammography, Tomography 110, etc. Imaging modalities such as ultrasound and MRI imaging 108 may generate images that are associated with "Elastograms". Elastography is a medical imaging modality that maps the elastic properties and stiffness of soft tissue. The hardness or softness of the tissue may provide diagnostic information about the presence or status of disease. For example, cancerous tumors may be harder than the surrounding tissue, and diseased livers may be stiffer than healthy ones. Ultrasound and MRI imaging 108 may be used to generate a stiffness map or elastogram, as well as an image of the tissue. Other imaging modalities, such as multiple imaging modalities 110, may not generate or be associated with elastograms, but may include information such as the "Applied Pressure", that is the amount of pressure being applied to the tissue during the imaging process.

Transformation processing 106 may include one or more learned transforms 112, as well as image processing routines 114. Transformation processing 106 may generate and/or learn one or more tissue transforms that model transformations to be applied to images of tissue based on compression of the tissue, which may be based on information such as elastograms, applied pressure, etc. The learned transforms 112 may be applied to input medical images 102 by image processing routines 114 to generate transformed output images 116.

Figure 2:
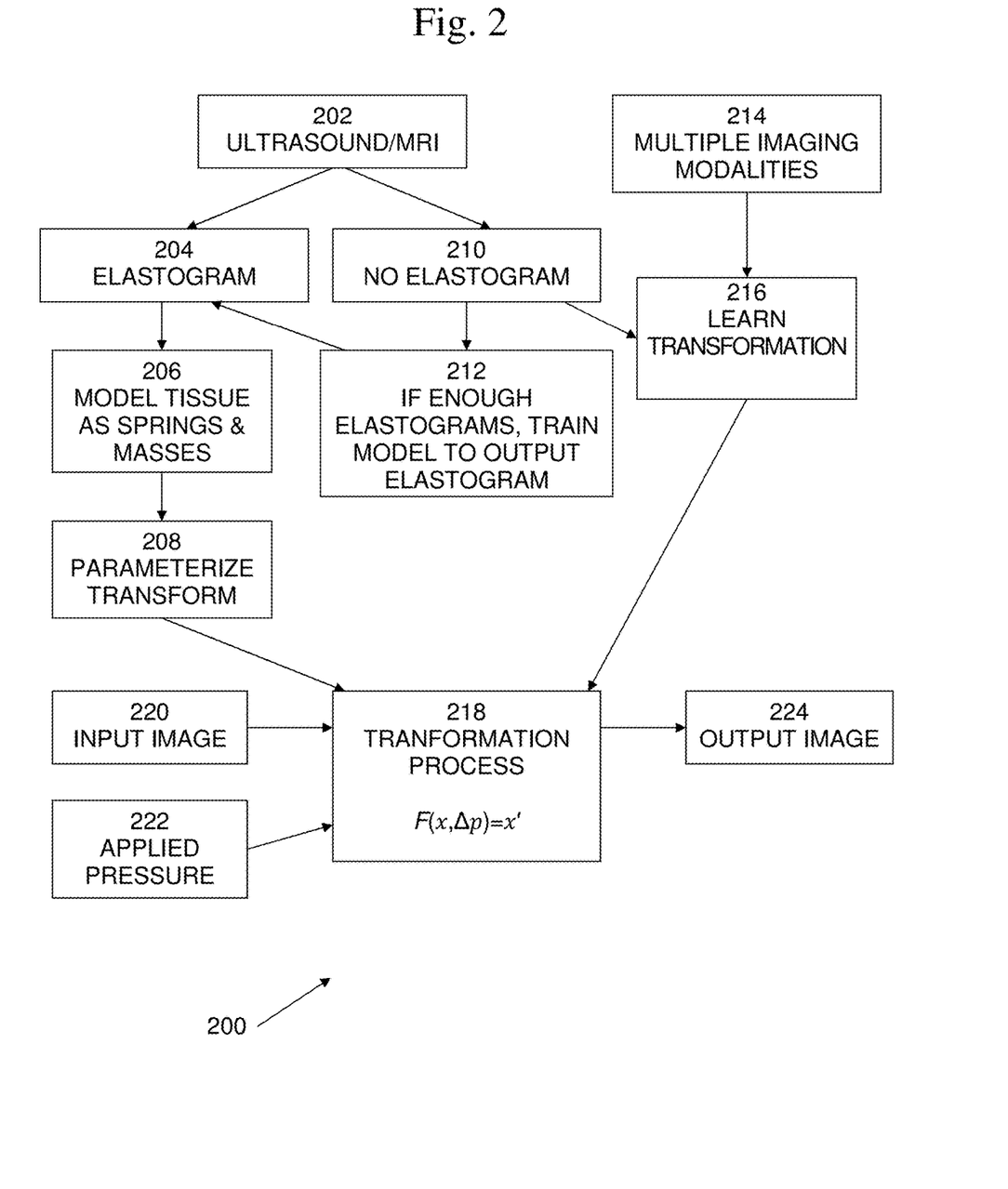
FIG. 2 is an exemplary flow diagram of processes for learning tissue elasticity-based transformations, according to embodiments of the present systems and methods.

Embodiments may use tissue elasticity-based transformation under applied force. Examples of processes 200 for generating such transformations are shown in FIG. 2. For example, at 202, imaging modalities 202 may incorporate an elastogram 204 aligned with the classification modality, such as Ultrasound and MRI images. At 206, the tissue may be modeled as a grid of springs and masses and at 208, the transform may be parameterized with initial displacement Δx (squeeze or stretch\skew). Thus, in the case where an elastogram is available, no transformation learning process is needed, as the transformation may be calculated directly using the masses and springs model at 206 and the parameterization at 208.

At 210, for ultrasound/MRI samples without elastograms and at 214, for images from imaging modalities that do not have elastograms, additional processing may be performed based on the nature of an additional dataset. For example, at 212, if there are enough pairs of elastograms available for the classification modality, even though elastograms may not be available for the particular input image 202, then a model may be trained that outputs an elastogram 204 based on the particular input image 202, which may then be used to generate transformation process using the masses and springs model at 206 and the parameteriztion at 208.

For modalities 214 that include multiple images from the same perspective but with varying pressure levels, for example, pairs of images of the same tissue from the same perspective but with varying amounts of pressure, at 216, the transformation: $F(x, \Delta p) = x'$ may be learned and incorporated into transformation process 218. In addition, images from modalities 214 should include or be associated with information indicating the applied pressure at which each image was obtained. In such embodiments, the learning procedure 216 may estimate a new image in the original modality, where the input is another image and the requested applied pressure difference. The choice between processes 212 and 216 may be based on the availability of data in addition to the images, and accordingly the performance of the models on these learning tasks. Both processes 212 and 216 may be implemented using existing deep learning architectures such as conditional generative adversarial networks, and conditional variational auto-encoders. These architectures are specifically designed to generate high dimensional data (such as a medical image in a specific modality), conditioned on some property (such as applied pressure, or the original image).

The parameterized transform 208, learned elasticity mapping 212, and/or learned transformation 216 may be mapped to a transformation process 218. An input image 220 and an applied pressure value 222 may be input to transformation process 218, which may apply the transformation process to input image 220 as determined by applied pressure value 222 and an output image 224 may be generated. It is to be noted that, in embodiments, input image 220, and ultrasound/MRI 202 may be the same image. In such an embodiment, learning the approximate elasticity mapping 212 may be done using a set of external images in a separate learning process.

Figure 3:
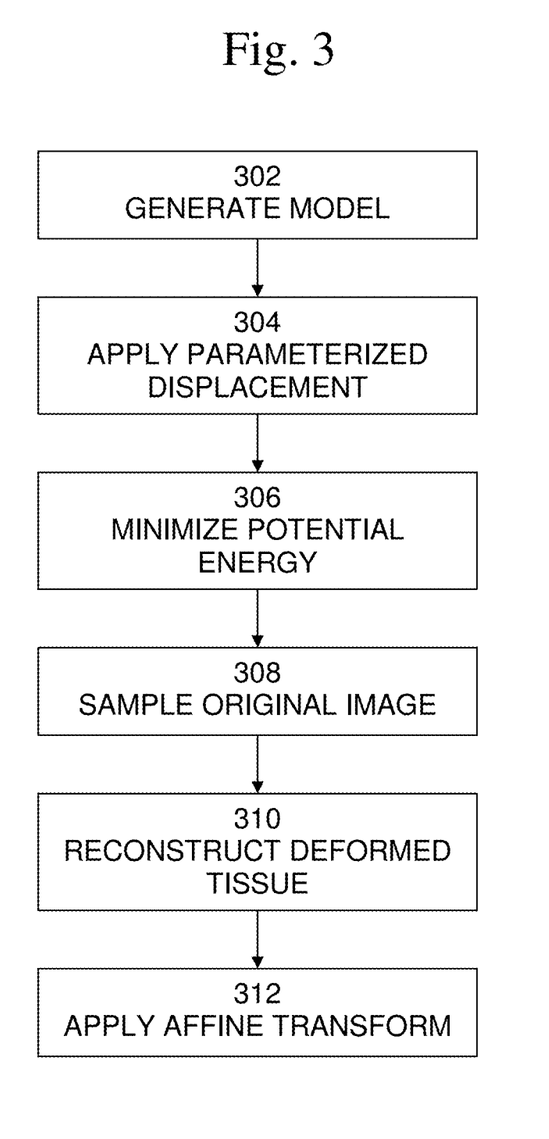
FIG. 3 is an exemplary flow diagram of a transformation process, according to embodiments of the present systems and methods.
Figure 4:
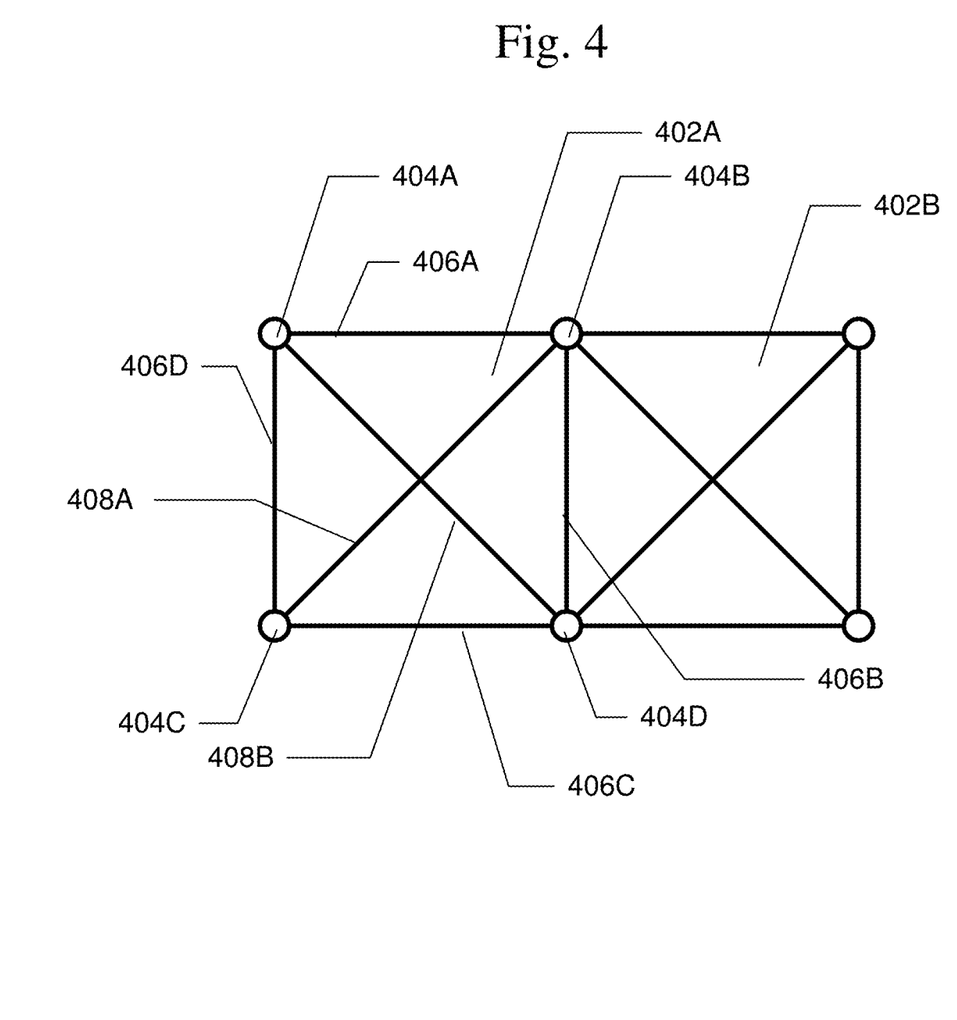
FIG. 4 is an exemplary diagram of a model of a rectangular grid of masses connected by springs, according to embodiments of the present systems and methods.

The transformation process 218 is shown in more detail in FIG. 3. In process 218, at 302, a model of the tissue in an image may be generated as a rectangular grid of masses connected by springs. Referring to FIG. 4, a model may be generated as, in each image of tissue, each rectangular connected group of pixels, such as 402A-B, may be represented by four masses, such as 404A-D, each mass located at a corner of each rectangular connected group of pixels. Four neutral springs 406A-D may connect the masses 404A-D, forming a rectangle. Two diagonal springs 408A-B may connect the masses 404A-D. Springs 408A-B may have spring coefficients proportional to the Young modulus of the tissue being imaged, which may be determined, for example, from the elastography information. The force applied by each spring 408A-B may be represented as $F=EA/L_0$ $\Delta L=k\Delta L$, where E is the Young modulus and A is the area of applied force F.

Once the model is generated, at 302, a parameterized displacement may be applied over the model rectangle grid with a constrained bottom. The rectangular cells 402A-B may be transformed (displaced) according to:

$$U(P_{i,j}) = -\frac{1}{2}\sum_{k,l \in R} K_{i,j,k,l}\left(l_{i,j,k,l} - l^0_{i,j,k,l} * \frac{l_{i,j,k,l}}{\|l_{i,j,k,l}\|}\right)^2,$$

which defines the internal energy applied over the (i,j) mass, where $K_{i,j,k,l}$ is the stiffness of the spring, and where R is the set of all neighboring masses (k,l). The displacement may satisfy 306, in which the total potential elastic energy may be minimized with respect to the positions of all masses, except the top and bottom masses, which induce the compressional pressure.

After the mass displacement is calculated, at 308, the original image 220 may be sampled on the new transformed grid cells. At 310, the image may be interpolated based on the transformed grid cells to reconstruct the deformed tissue. At 312, an affine transform may be applied on patches related to each grid element, such as the grid element and the immediately adjacent grid elements. This results in an output image 224 being generated.

Figure 5:
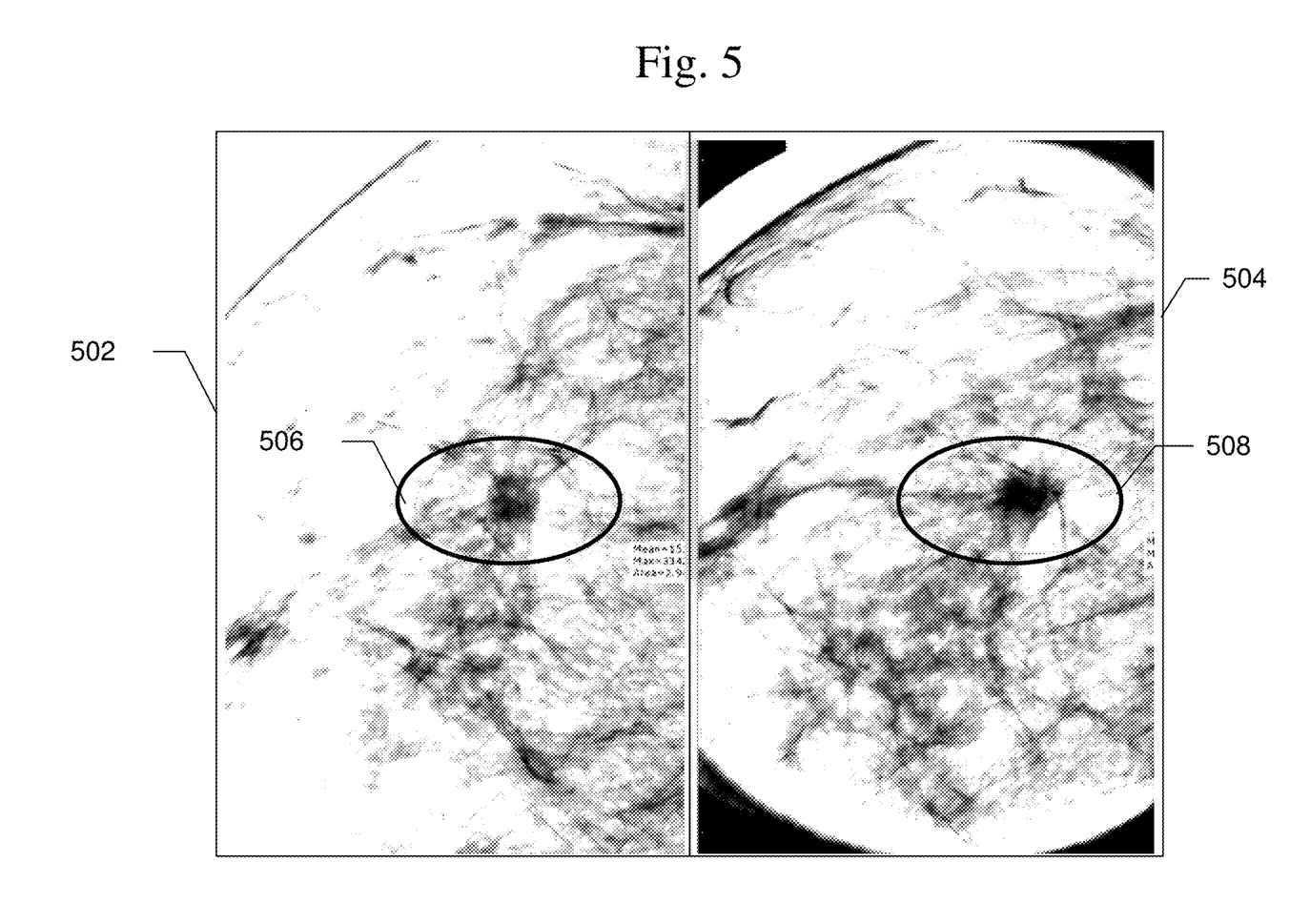
FIG. 5 is an exemplary illustration of compression variance on mammography, according to embodiments of the present systems and methods.

An example of compression variance on mammography according to embodiments of the present systems and methods is shown in FIG. 5. In the example shown in FIG. 5, mammogram image 502 shows an image before compression, while mammogram image 504 shows an image after compression. As can be seen in this example, the appearance of feature 506 may change 508 when compression is applied.

Figure 6:
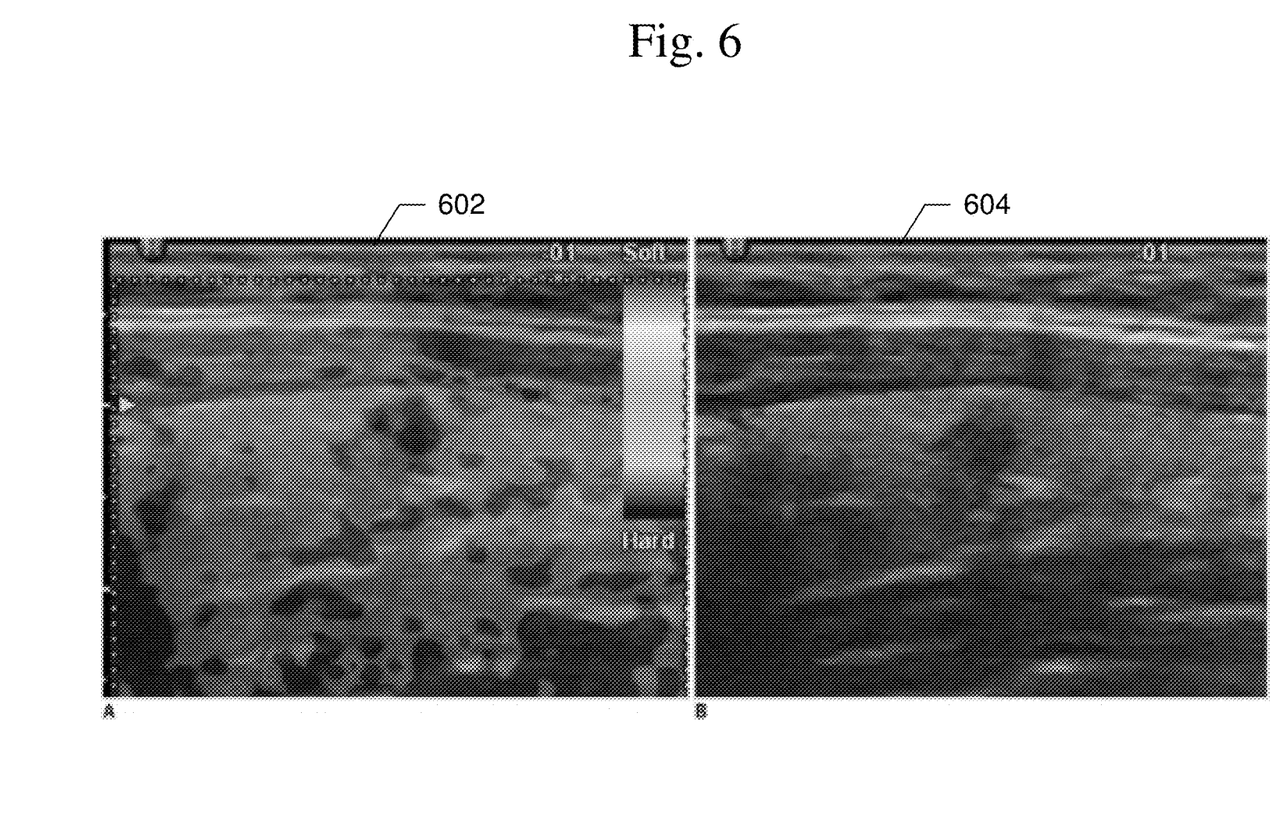
FIG. 6 is an exemplary illustration of ultrasound elastography of thyroid nodules, according to embodiments of the present systems and methods.

An example of ultrasound elastography of thyroid nodules according to embodiments of the present systems and methods is shown in FIG. 6. In the example shown in FIG. 6, ultrasound image 602 shows the compressibility of tissue features, while ultrasound image 604 shows an image after compression. The appearances of features may change when compression is applied, depending upon their compressibility.

Figure 7:
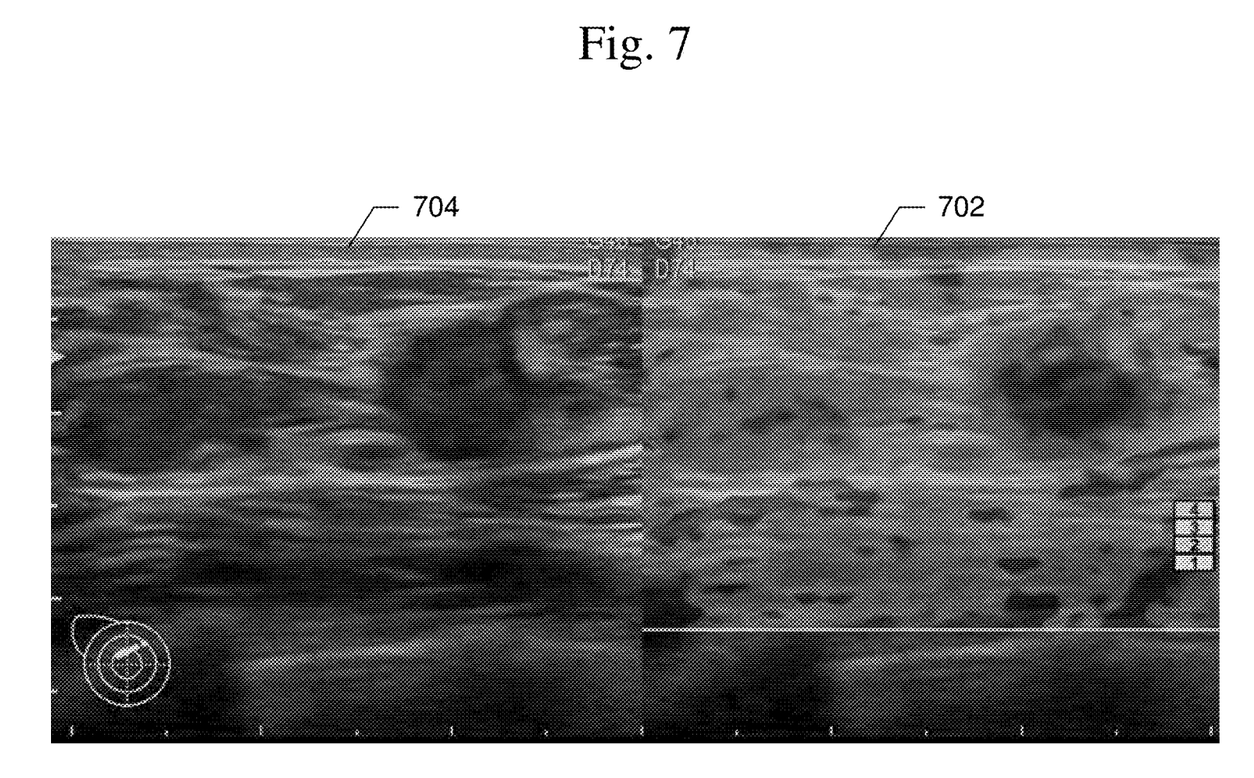
FIG. 7 is an exemplary illustration of ultrasound elastography of fibroadenoma and infiltrating ductal carcinoma, according to embodiments of the present systems and methods.

An example of ultrasound elastography of fibroadenoma and infiltrating ductal carcinoma according to embodiments of the present systems and methods is shown in FIG. 7. In the example shown in FIG. 7, ultrasound image 702 shows the compressibility of tissue features, with the carcinoma being relatively non-compressible and the fibroadenoma being relatively compressible, while ultrasound image 704 shows an image after compression. The appearances of features may change when compression is applied, depending upon their compressibility.

Embodiments of the present systems and methods may incorporate physiological knowledge and thus enrich the given dataset. Embodiments do not require a large labeled data when learning a transformation. Embodiments may be applicable to a variety of imaging modalities and may utilize prior knowledge of the dynamics of physiological systems to analytically generate augmented samples for machine learning.

Figure 8:
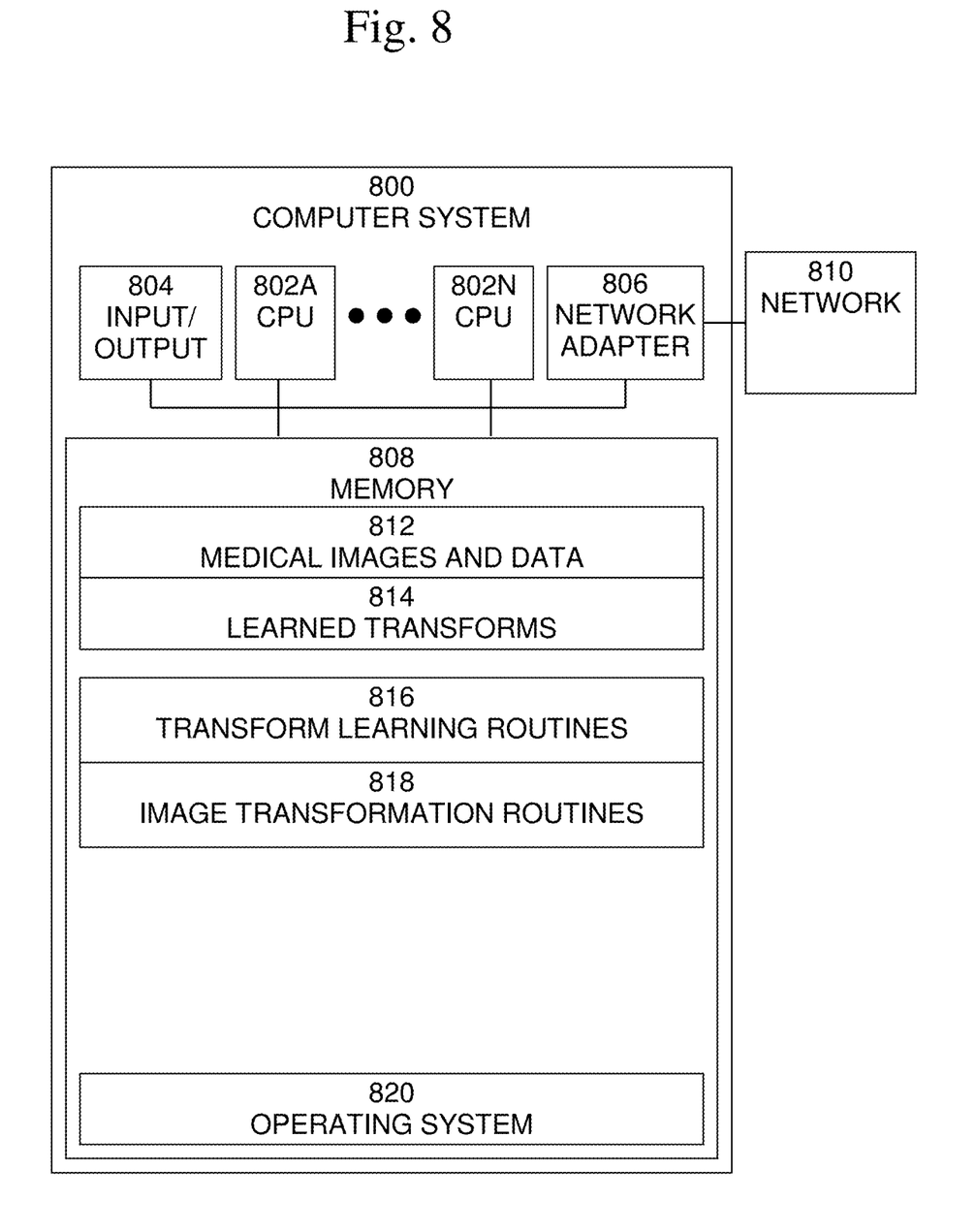
FIG. 8 is an exemplary block diagram of a computer system, in which processes involved in the embodiments described herein may be implemented.

An exemplary block diagram of a computer system 800, in which processes involved in the embodiments described herein may be implemented, is shown in FIG. 8. Computer system 800 may be implemented using one or more programmed general-purpose computer systems, such as embedded processors, systems on a chip, personal computers, workstations, server systems, and minicomputers or mainframe computers, or in distributed, networked computing environments. Computer system 800 may include one or more processors, such as general purpose central processing units (CPUs), graphics processing units (GPUs), special purpose processing units, etc. 802A-802N, input/output circuitry 804, network adapter 806, and memory 808. In embodiments, processing according to the present systems and methods may be formulated for processing by any of CPUs, GPUs, special purpose processing units, etc. For simplicity, all such processing units may be referred to herein as CPUs. CPUs 802A-802N execute program instructions in order to carry out the functions of the present communications systems and methods. Typically, CPUs 802A-802N are one or more microprocessors, such as an INTEL CORE® processor. FIG. 8 illustrates an embodiment in which computer system 800 is implemented as a single multi-processor computer system, in which multiple processors 802A-802N share system resources, such as memory 808, input/output circuitry 804, and network adapter 806. However, the present communications systems and methods also include embodiments in which computer system 800 is implemented as a plurality of networked computer systems, which may be single-processor computer systems, multi-processor computer systems, or a mix thereof.

Input/output circuitry 804 provides the capability to input data to, or output data from, computer system 800. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 806 interfaces device 800 with a network 810. Network 810 may be any public or proprietary LAN or WAN, including, but not limited to the Internet.

Memory 808 stores program instructions that are executed by, and data that are used and processed by, CPU 802 to perform the functions of computer system 800. Memory 808 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 808 may vary depending upon the function that computer system 800 is programmed to perform. In the example shown in FIG. 8, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present communications systems and methods may include any and all such arrangements.

In the example shown in FIG. 8, memory 808 may include medical images and data 812, learned transforms 814, transform learning routines 816, and image transformation routines 818, and operating system 820. Medical images and data 812 may include medical images generated by, for example, ultrasound and MRI imaging and multiple imaging modalities, such as Mammography, Tomography, etc., as well as data associated with such images, such as elastograms, applied pressure information, etc. Learned transforms 814 may include one or more tissue transforms that model transformations to be applied to images of tissue based on compression of the tissue, which may be based on information such as elastograms, applied pressure, etc. Transform learning routines 816 may include software routines to generate learned transforms 814, as described above. Image transformation routines 818 may include software routines to apply learned transforms 814 to input medical images included in 812 and generate transformed output images. Operating system routines 822 may provide additional system functionality.

As shown in FIG. 8, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multi-tasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method implemented in a computer system comprising a processor, memory accessible by the processor, and computer program instructions stored in the memory and executable by the processor, the method comprising:

generating, at the computer system, a transform for an image of tissue based on deformation of the tissue under compression, wherein when an imaging modality generates the image of the tissue without an associated elastogram, the transform is generated by:
   generating an elastogram based on reference images with exemplary elastograms;
   modeling the tissue as a rectangular grid of masses connected by springs based on the generated elastogram; and
   generating a displacement over the rectangular grid with a constrained bottom, wherein the displacement minimizes a total potential elastic energy with respect to positions of all the masses, except top and bottom masses, which induce compressional pressure;

obtaining, at the computer system, an image of tissue using the imaging modality; and generating, at the computer system, an output image by transforming the image of the tissue using the transform.

2. The method of claim 1, wherein when the imaging modality generates the image of the tissue with the associated elastogram the transform is generated by:
   modeling the tissue as the rectangular grid of masses connected by the springs based on the associated elastogram; and
   generating the displacement over the rectangular grid with the constrained bottom, wherein the displacement minimizes the total potential elastic energy with respect to the positions of all the masses, except the top and bottom masses, which induce the compressional pressure.

3. The method of claim 1, wherein the imaging modality comprises one of ultrasound or magnetic resonance imaging.

4. The method of claim 1, wherein the output image is further generated based on information indicating a pressure applied to the tissue during acquisition of the image of the tissue.

5. The method of claim 1, wherein the imaging modality comprises one of mammography or tomography.

6. A system comprising a processor, memory accessible by the processor, and computer program instructions stored in the memory and executable by the processor to perform:

generating, at the computer system, a transform for an image of tissue based on deformation of the tissue under compression, wherein when an imaging modality generates the image of the tissue without an associated elastogram, the transform is generated by:
   generating an elastogram based on reference images with exemplary elastograms;
   modeling the tissue as a rectangular grid of masses connected by springs based on the generated elastogram; and
   generating a displacement over the rectangular grid with a constrained bottom, wherein the displacement minimizes a total potential elastic energy with respect to positions of all the masses, except top and bottom masses, which induce compressional pressure;

obtaining, at the computer system, an image of tissue using the imaging modality; and generating, at the computer system, an output image by transforming the image of the tissue using the transform.

7. The system of claim 6, wherein when the imaging modality generates the image of the tissue with the associated elastogram the transform is generated by:
- modeling the tissue as the rectangular grid of masses connected by the springs based on the associated elastogram; and
- generating the displacement over the rectangular grid with the constrained bottom, wherein the displacement minimizes the total potential elastic energy with respect to the positions of all the masses, except the top and bottom masses, which induce the compressional pressure.

8. The system of claim 6, wherein the imaging modality comprises one of ultrasound or magnetic resonance imaging.

9. The system of claim 6, wherein the output image is further generated based on information indicating a pressure applied to the tissue during acquisition of the image of the tissue.

10. The system of claim 6, wherein the imaging modality comprises one of mammography or tomography.

11. A computer program product comprising a non-transitory computer readable storage having program instructions embodied therewith, the program instructions executable by a computer, to cause the computer to perform a method comprising:
- generating, at the computer system, a transform for an image of tissue based on deformation of the tissue under compression, wherein when an imaging modality generates the image of the tissue without generating an associated elastogram the transform is generated by:
  - generating an elastogram based on reference images with exemplary elastograms;
  - modeling the tissue as a rectangular grid of masses connected by springs based on the generated elastogram; and
  - generating a displacement over the rectangular grid with a constrained bottom, wherein the displacement minimizes a total potential elastic energy with respect to positions of all the masses, except top and bottom masses, which induce compressional pressure;
- obtaining, at the computer system, an image of tissue using the imaging modality; and
- generating, at the computer system, an output image by transforming the image of the tissue using the transform.

12. The computer program product of claim 11, wherein when the imaging modality generates the image of the tissue with the associated elastogram the transform is generated by:
- modeling the tissue as the rectangular grid of masses connected by the springs based on the associated elastogram; and
- generating the displacement over the rectangular grid with the constrained bottom, wherein the displacement minimizes the total potential elastic energy with respect to the positions of all the masses, except the top and bottom masses, which induce the compressional pressure.

13. The computer program product of claim 11, wherein the imaging modality comprises one of ultrasound or magnetic resonance imaging.

14. The computer program product of claim 11, wherein the output image is further generated based on information indicating a pressure applied to the tissue during acquisition of the image of the tissue.

* * * * *